US006518421B1

(12) United States Patent
Li et al.

(10) Patent No.: US 6,518,421 B1
(45) Date of Patent: Feb. 11, 2003

(54) PROCESS FOR THE PREPARATION OF EPOTHILONE ANALOGS

(75) Inventors: Wen Sen Li, Holmdel, NJ (US); John E. Thornton, Newtown, PA (US); Zhenrong Guo, East Brunswick, NJ (US); Shankar Swaminathan, Monmouth Junction, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 09/775,361

(22) Filed: Feb. 1, 2001

Related U.S. Application Data

(63) Continuation-in-part of application No. 09/528,526, filed on Mar. 20, 2000.

(51) Int. Cl.$^7$ ...................... C07D 491/00; C07D 417/00
(52) U.S. Cl. ....................................... 540/462; 548/181
(58) Field of Search ........................... 540/462; 548/181

(56) References Cited

U.S. PATENT DOCUMENTS

| 6,194,181 B1 | 2/2001 | Hofmann et al. ........... 435/118 |
| 6,204,388 B1 | 3/2001 | Danishefsky et al. ....... 546/340 |
| 6,211,412 B1 | 4/2001 | Georg et al. ................ 568/309 |

FOREIGN PATENT DOCUMENTS

| DE | 4138042.8 | 5/1993 |
| DE | 19542986.9 | 5/1997 |
| DE | 19639456.2 | 5/1997 |
| DE | 19636343.8 | 3/1998 |
| DE | 19645361.5 | 4/1998 |
| DE | 19645362.3 | 4/1998 |
| DE | 19647580.5 | 5/1998 |
| DE | 19701758 | 7/1998 |
| DE | 1970705.3 | 9/1998 |
| DE | 19713970 | 10/1998 |
| DE | 19720312 | 11/1998 |
| DE | 19821954 | 11/1998 |
| DE | 19726627 | 12/1998 |
| EP | 879 605 | 11/1998 |
| WO | 93/10121 | 5/1993 |
| WO | 97/19086 | 5/1997 |
| WO | 98/08849 | 3/1998 |
| WO | 98/22461 | 5/1998 |
| WO | 98/24427 | 6/1998 |
| WO | 98/25929 | 6/1998 |
| WO | 98/38192 | 9/1998 |
| WO | 98/47891 | 10/1998 |
| WO | 99/01124 | 1/1999 |
| WO | 99/02514 | 1/1999 |
| WO | 99/03848 | 1/1999 |
| WO | 99/07692 | 2/1999 |
| WO | 99/39694 | 8/1999 |
| WO | 99/42602 | 8/1999 |
| WO | 99/43320 | 9/1999 |
| WO | 99/43653 | 9/1999 |
| WO | 99/67252 | 12/1999 |
| WO | 00/00485 | 1/2000 |
| WO | 00/31247 | 6/2000 |
| WO | 00/37473 | 6/2000 |
| WO | 00/49021 | 8/2000 |
| WO | 00/66589 | 11/2000 |

OTHER PUBLICATIONS

Altmann, K.H., et al., "Epothilones and Related Structures—A New Class of Microtubule Inhibitors With Patent In Vivo Antitumor Activity," Biochim. Biophys Acta, 1470 (2000).

Nicolaou et al., "Total Synthesis of Epothilone E and Analogs with Modified Side Chains Through The Stille Coupling Reaction", Angew. Chem. Int. Ed. 37, 84–87 (1998).

Nicolaou et al., "Total Synthesis of Oxazole– and Cyclopropane–Containing Epothilone B Analogues by the Macrolactonization Approach", Chemistry, European Journal, vol. 3, No. 12, 1761–1986 (1997).

Nicolaou et al., "Chemical Biology of Epothilones", Angew. Chem. Int. Ed., 37, 2014–2045 (1988).

Balog, A., et al., "Total Synthesis of (–)–Epothilone A", Angew. Chem. Int. Ed. Engl., vol. 35, No. 23/24, 2801–2803 (1996).

Bertini, F., et al., "Alkenes from Epoxides by Reductive Elimination with Magnesium Bromide–Magnesium Amalgam", Chem. Commun. , 144 (1970).

Bollag, D.M., et al., "Epothilones, A New Class of Microtubule–stabilizing Agents with a Taxol–like Mechanism of Action", Cancer Res. 55, No. 11, 2325–2333 (1995).

Fujisawa, T., et al., "Deoxygenation of Epoxides to Olefins with $FeCl_3$—n–BuLi System", Chem. Lett., 883–886 (1974).

Fujiwara, Y., et al., "Reductive Coupling of Carbonyl Compounds to Olefins by Tungsten Hexachloride–Lithium Aluminum Hydride and Some Tungsten and Molybdenum Carbonyls", J. Org. Chem., vol. 43, No. 12, 2477–2479 (1978).

Gladysz, J. A., et al., "Deoxygenation of Epoxides by Metal Atom Cocondensation", J. Org. Chem., vol. 41, No. 22, 3647–3648 (1976).

Hofle, G., et al., "Epothilone A and B—Novel 16–Membered Macrolides with Cytotoxic Activity: Isolation, Crystal Structure, and Conformation in Solution", Angew. Chem. Int. Ed. Engl., vol. 35, No. 13/14, 1567–1569 (1996).

Hofle, G., et al., "N–Oxidation of Epothilone A–C and O–Acyl Rearrangement to C–19 and C–21—Substituted Epothilones", Angew. Chem. Int. Ed., vol. 38, No. 13/14, 1971–1974 (1999).

(List continued on next page.)

Primary Examiner—Bruck Kifle
(74) Attorney, Agent, or Firm—Rena Patel

(57) ABSTRACT

The present invention relates to a process for the preparation of epothilone analogs by initially forming novel ring-opened epothilones and carrying out a macrolactamization reaction thereon. The subject process is amenable to being carried out in a single reaction vessel without isolation of the intermediate compound and provides at least about a three-fold increase in yield over prior processes for preparing the desired epothilone analogs.

28 Claims, No Drawings

OTHER PUBLICATIONS

Inokuchi, T., et al., "Opening of Epoxides to Olefins or Halohydrins with Vanadium(II)–Tetrahydrofuran or Vanadium(III)–Tetrahydrofuran Complexes", *Synlett*, No. 6, 510–512 (1992).

Kowalski. R. J., et al., "Activities of the Microtubule–stabilizing Agents Epothilones A and B with Purified Tubulin and in Cells Resistant to Paclitaxel (Taxol®)" *J. Biol. Chem.*, vol. 272, No. 4, 2534–2541 (1997).

Kupchan, S. M., et al., "Reductive Elimination of Epoxides to Olefins with Zinc–Copper Couple", *J. Org. Chem.*, vol. 36, No. 9, 1187–1190 (1971).

Martin, M. G., et al., "Epoxides as Alkene Protecting Groups. A Mild and Efficient Deoxygenation", *Tetrahedron Letters*, vol. 25, No. 3, 251–254 (1984).

McMurry, J. E., et al., "Reduction of Epoxides to Olefins with Low Valent Titanium", *J. Org. Chem.*, vol. 40, No. 17, 2555–2556 (1975).

McMurry, J. E., et al., "Some Deoxygenation Reactions with Low–Valent Titanium ($TiCl_3/LiAlH_4$", *J. Org. Chem.*, vol. 43, No. 17, 3249–3254 (1978).

Meng, D., et al., "Remote Effects in Macrolide Formation Through Ring–Forming Olefin Metathesis: An Application to the Synthesis of Fully Active Epothilone Congeners", *J. Am. Chem. Soc.*, vol. 119, No. 11, 2733–2734 (1997).

Nicolaou, K. C., et al., "An Approach to Epothilones Based on Olefin Metathesis", *Angew. Chem. Int. Ed. Engl.*, vol. 35, No. 20, 2399–2401 (1996).

Nicolaou, K. C., et al., "Total Synthesis of Epothilone A: The Macrolactonization Approach", *Angew. Chem. Int. Ed. Engl.*, vol. 36, No. 5, 525–527 (1997).

Nicolaou, K. C., et al., "Designed Epothilones: Combinatorial Synthesis, Tubulin Assembly Properties, and Cytotoxic Action against Taxol–Resistant Tumor Cells", *Angew. Chem. Int. Ed. Engl.*, vol. 36, No. 19, 2097–2103 (1997).

Nicolaou, K.C., et al., "The Olefin Metathesis Approach to Epothilone A and Its Analogues", *J. Am. Chem. Soc.*, vol. 119, No. 34, 7960–7973 (1997).

Nicolaou, K. C., et al., "Total Syntheses of Epothilones A and B via a Macrolactonization–Based Strategy", *J. Am. Chem. Soc.*, vol. 119, No. 34, 7974–7991 (1997).

Nicolaou, K. C., et al., "Synthesis of Epothilones A and B in Solid and Solution Phase", *Nature*, vol. 387, 268–272 (1997).

Nicolaou, K. C., et al., "Synthesis of Epothilones A and B in Solid and Solution Phase" (Correction to *Nature* 387, 268–272 (1997)), *Nature*, 390, 100 (1997).

Raucher, S., et al., "Total Synthesis of (+)–Dihydrocostunolide via Tandem Cope–Claisen Rearrangement", *J. Org. Chem.*, vol. 51, No. 26, 5503–5505 (1986).

Sato, M, et al., "Reduction of Organic Compounds with Low–Valent Niobium ($NbCl_5/NaAlH_4$)", *Chem. Letters*, 157–160 (1982).

Schinzer, D., et al., "Total Synthesis of (–)–Epothilone A", *Angew. Chem. Int. Ed. Engl.*, vol. 36, No. 5, 523–524 (1997).

Schobert, R., et al., "Reduction and Isomerization of Oxiranes and α–Diazoketones by Various Early Transition Metallocenes", *Synlett*, vol. 8, 465–466 (1990).

Sharpless, K. B., et al., "Lower Valent Tungsten Halides. A New Class of Reagents for Deoxygenation of Organic Molecules", *J. Amer. Chem. Soc.*, vol. 94, No.18, 6538–6540 (1972).

Su, D.–S., et al., "Total Synthesis of (–)–Epothilone B: An Extension of the Suzuki Coupling Method and Insights into Structure–Activity Relationships of the Epothilones", *Angew. Chem. Int. Ed. Engl.*, vol. 36, No. 7, 757–759 (1997).

Su, D.–S., et al., "Structure–Activity Relationships of the Epothilones and the First In Vivo Comparison with Paclitaxel", *Angew. Chem. Int. Ed. Engl.*, vol. 36, No. 19, 2093–2096 (1997).

Victory, S. F., et al., "Relative Stereochemistry and Solution Conformation of the Novel Paclitaxel–Like Antimitotic Agent Epothilone A", *Bioorg. Med. Chem. Letts.*, vol. 6., No. 7, 893–898 (1996).

Winkler, J. D., et al., "A Model For The Taxol (Paclitaxel)/Epothilone Pharmacophore", *Bioorg. Med. Chem. Letts.*, vol. 6, No. 24, 2963–2966 (1996).

Yang, Z., et al., "Total Synthesis of Epothilone A: The Olefin Metathesis Approach", *Angew. Chem. Int. Ed. Engl.*, vol. 36, No. 1/2, 166–168 (1997).

Bollag, D., et al., "Epothilone, A New Structural Class of Microtubule Stabilizer", Abstract, *Proc. Am. Assoc. Cancer Res.*, vol. 36, 86 Meet. 454 (1995).

Bollag, D., "Epothilones: Novel Microtubule–Stabilising Agents", *Expert Opin. Invest. Drugs*, vol. 6, No. 7, 867–873 (1997).

Bertinato, P., et al., "Studies Toward a Synthesis of Epothilone A: Stereocontrolled Assembly of the Acyl Region and Models for Macrocyclization", J. Org. Chem., vol. 61, No. 23, 8000–8001 (1996).

*Chemical & Engineering News*, "Epothilone Epiphany: Total Syntheses", vol. 74, No. 52, 24–26 (1996).

*Chemical & Engineering News*, "First Total Synthesis of Epothilone B", vol. 75, No. 13, 23 (1997).

*Chemical & Engineering News*, "Solid–Phase Epothilone Synthesis Used to Create Analog Library", vol. 75, No. 20, 33 (1997).

Claus, E., et al., "Synthesis of the C1–C9 Segment of Epothilons", *Tetrahedron Lett.*, vol. 38, No. 8, 1359–1362 (1997).

De Brabander, J., et al., "Towards a Synthesis of Epothilone A: Rapid Assembly of the C1–C6 and C7–C12 Fragments", *Synlett*, vol. 7, 824–826 (1997).

Gabriel, T. and Wessjohann, L., "The Chromium–Reformatsky Reaction: Asymmetric Synthesis of the Aldol Fragment of the Cytotoxic Epothilons from 3–(2–Bromoacyl)–2–Oxazolidinones", *Tetrahedron Lett.*, vol. 38, No. 8, 1363–1366 (1997).

Gerth, K., et al., "Epothilons A and B: Antifungal and Cytotoxic Compounds from *Sorangiusm cellulosum* (Myxobacteria) Production, Physico–chemical and Biological Properties", *J. Antibiotics*, vol. 49, No. 6, 560–563 (1996).

Marshall, A., "Total Synthesis of Epothilone", *Nature Biotechnology*, vol. 15, No. 3, 205 (1997).

Meng, D., et al., "Studies Toward a Synthesis of Epothilone A: Use of Hydropyran Templates for the Management of Acyclic Stereochemical Relationships", *J. Org. Chem.*, vol. 61, No. 23, 7998–7999 (1996).

Meng, D., et al., "Total Syntheses of Epothilones A and B", *J. Am. Chem. Soc.*, vol. 119, No. 42, 10073–10092 (1997).

Mensching, S. and Kalesse, M., "Generation of Thiazoles by Column Dehydrogenation of Thiazolidines with $MnO_2$", *J. Prakt. Chem.*, vol. 339, No. 1, 96–97 (1997).

Mulzer, J. and Mantoulidis, A., "Synthesis of the C(1)–C(9) Segment of the Cytotoxic Macrolides Epothilon A and B", *Tetrahedron Lett.,* vol. 37, No. 51, 9179–9182 (1996).

Nicolaou, K., et al., "Chemistry, Biology and Medicine of Selected Tubulin Polymerizing Agents", *Pure Appl. Chem.,* vol. 71, No. 6, 989–997 (1999).

Nicolaou, K., et al., "Total Synthesis of Epothilone E and Related Side–chain Modified Analogues Via a Stille Coupling Based Strategy", *Bioorg. Med. Chem.,* vol. 7, No. 5, 665–697 (1999).

Schinzer, D., et al., "Studies Towards the Total Synthesis of Epothilones: Asymmetric Synthesis of the Key Fragments", *Chem. Eur. J.,* vol. 2, No. 22, 1477–1482 (1996).

Taylor, R. and Haley, J., "Towards the Synthesis of Epothilone A: Enantioselective Preparation of the Thiazole Sidechain and Macrocyclic Ring Closure", *Tetrahedron Lett.,* vol. 38, No. 12, 2061–2064 (1997).

Schinzer, D., et al., "Syntheses of (–)–Epothilone A", *Chem. Eur. J.,* vol. 5, No. 9, 2483–2491 (1999).

Schinzer, D., et al., "Syntheses of (–)–Epothilone B", *Chem. Eur. J.,* vol. 5, No. 9, 2492–2500 (1999).

Nicolaou, K. C., et al., "Synthesis and Biological Properties of C12,13–Cyclopropylepothilone A and Related Epothilones", *Chemistry & Biology,* vol. 5, No. 7, 365–372 (1998).

PROCESS FOR THE PREPARATION OF EPOTHILONE ANALOGS

CROSS-REFERENCE TO RELATED APPLICATIONS

This application is a continuation-in-part patent application of co-pending U.S. application Ser. No. 09/528,526, filed on Mar. 20, 2000.

FIELD OF THE INVENTION

The present invention relates to an improved process for the preparation of certain epothilone analogs, including novel intermediates, which is characterized by a significantly enhanced yield.

BACKGROUND OF THE INVENTION

Epothilones are macrolide compounds that find utility in the pharmaceutical field. For example, epothilones A and B having the structures:

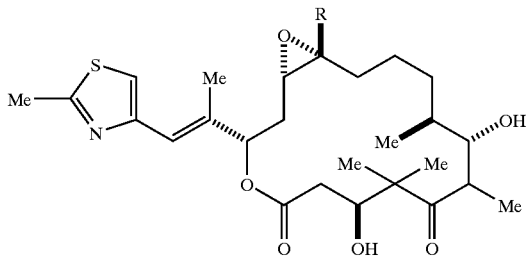

epothilone A R=H
epothilone B R=Me may be found to exert microtubule-stabilizing effects similar to paclitaxel (TAXOL®) and hence cytotoxic activity against rapidly proliferating cells, such as, tumor cells or other hyperproliferative cellular disease, see Hofle, G., et al., *Angew. Chem. Int. Ed. Engl.*, Vol. 35, No.13/14, 1567–1569 (1996); WO93/10121 published May 27, 1993; and WO97/19086 published May 29, 1997.

Derivatives and analogs of epothilones A and B have been synthesized and may be used to treat a variety of cancers and other abnormal proliferative diseases. Such analogs are disclosed in Hofle et al., Id.; Nicolaou, K. C., et al., *Angew. Chem. Int. Ed. Engl.*, Vol. 36, No. 19, 2097–2103 (1997); and Su, D.-S., et al., *Angew. Chem. Int. Ed. Engl.*, Vol. 36, No. 19, 2093–2097 (1997).

Analogs of the epothilones that have been found to have advantageous activity are represented by the following structure

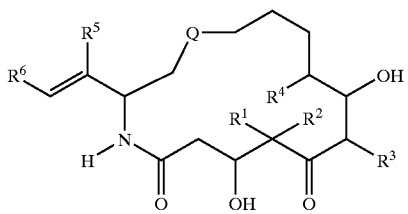

II wherein Q, and $R^1$ through $R^6$ have the meanings given herein below. An improved synthesis for these analogs involving novel intermediates is provided in accordance with the present invention.

SUMMARY OF THE INVENTION

The present invention is directed to a process for the preparation of compounds represented by formulas I and II wherein Q, Z, and $R^1$ through $R^6$ are as defined below.

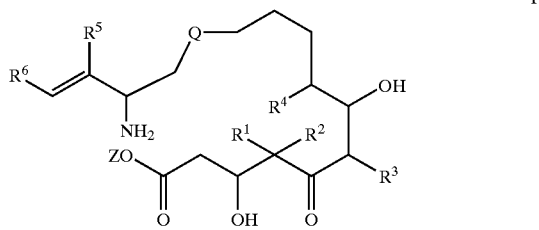

I

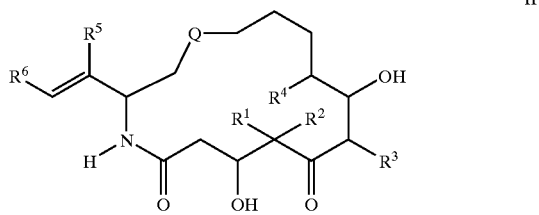

II

The compounds represented by formula I are novel intermediates for the preparation of epothilone analogs that are useful in the treatment of a variety of cancers and other abnormal proliferative diseases. Compounds represented by formula I may be utilized to prepare epothilone analogs represented by formula II which are useful as anticancer agents.

DETAILED DESCRIPTION OF THE INVENTION

The process of the present invention provides an advantageous synthesis for the compounds represented by formula II including the preparation of novel ring opened epothilone intermediate compounds represented by formula I.

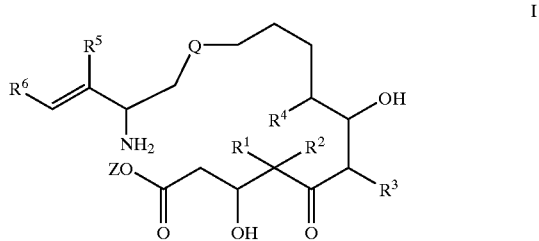

I

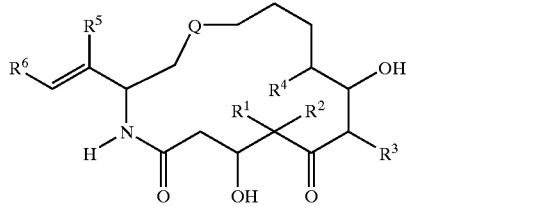

II

As used in formulas I and II, and throughout the specification, the meaning of the symbol Q is:

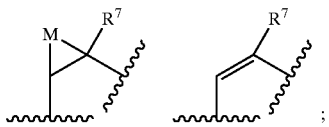

M is selected from the group consisting of oxygen, sulfur, $NR^8$, and $CR^9R^{10}$;

Z is selected from the group consisting of

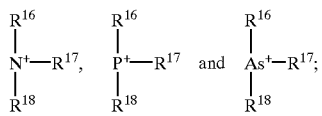

$R^1$–$R^5$, $R^7$, and $R^{11}$–$R^{15}$ are selected from the group consisting of hydrogen, alkyl, substituted alkyl, aryl, substituted aryl and heterocyclo, and wherein $R^1$ and $R^2$ are alkyl, they can be joined to form a cycloalkyl;

$R^6$ is selected from the group consisting of hydrogen, alkyl, substituted alkyl, aryl, substituted aryl, cycloalkyl, heterocyclo and substituted heterocyclo;

$R^8$ is selected from the group consisting of hydrogen, alkyl, substituted alkyl, $R^{11}C=O$, $R^{12}OC=O$ and $R^{13}SO_2$;

$R^9$ and $R^{10}$ are selected from the group consisting of hydrogen, halogen, alkyl, substituted alkyl, aryl, heterocyclo, hydroxy, $R^{14}C=O$, and $R^{15}OC=O$; and $R^{16}$, $R^{17}$, and $R^{18}$ are independently selected from the group consisting of alkyl, aryl, and aralkyl.

The process of the present invention is advantageous in that only two steps are required to prepare the epothilone analogs from the epothilone starting material, for example, epothilone B. Two further distinct advantages of the process of the present invention are that the yields of crystallized compounds represented by formula II are significantly higher than those previously realized utilizing the free acid of the compound represented by formula I as the intermediate compound, and the fact that the preparation of the intermediate is amendable to being carried out in one step. A further advantage of this process is that it can progress from the epothilone starting material to the epothilone represented by formula II without the need to isolate and purify an intermediate. Those skilled in the art will immediately recognize the economic benefits of such a process.

Definitions

The following are definitions of various terms used herein to describe this invention. These definitions apply to the terms as they are used throughout this specification, unless otherwise limited in specific instances, either individually or as part of a larger group.

The term "epothilone", as used herein, denotes compounds containing an epothilone core and a side chain group as defined herein. The term "epothilone core", as used herein, denotes a moiety containing the core structure (with the numbering of ring system positions used herein shown):

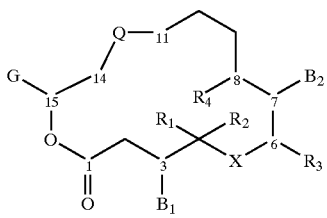

wherein the substituents are as defined herein and where
X is selected from the group consisting of C=O, $CH_2$ and $CHOR^{19}$;
$B^1$ and $B^2$ are selected from the group consisting of $OR^{20}$ and $OCOR^{21}$;
$R^{19}$ and $R^{20}$ are selected from the group consisting of hydrogen, alkyl, substituted alkyl, trialkylsilyl, alkyldiarylsilyl, and dialkylarylsilyl; and
$R^{21}$ is selected from the group consisting of hydrogen, alkyl, substituted alkyl, aryl, and heterocyclo.

The term "side chain group" refers to substituent G as defined by the following formula $$Y_m-A-$$

where
A is optionally substituted alkenyl;
Y is an optionally substituted ring system containing one to three rings and at least one carbon to carbon double bond in at least one ring; and
m is zero or 1.

The term "alkyl" refers to optionally substituted straight- or branched-chain saturated hydrocarbon groups having from 1 to 20 carbon atoms, preferably from 1 to 7 carbon atoms. The expression "lower alkyl" refers to optionally substituted alkyl groups having from 1 to 4 carbon atoms.

The term "substituted alkyl" refers to an alkyl group substituted by, for example, one to four substituents, such as, halo, trifluoromethyl, trifluoromethoxy, hydroxy, alkoxy, cycloalkyoxy, heterocylooxy, oxo, alkanoyl, aryl, aryloxy, aralkyl, alkanoyloxy, amino, alkylamino, arylamino, aralkylamino, cycloalkylamino, heterocycloamino, disubstituted amino in which the two substituents on the amino group are selected from alkyl, aryl, aralkyl, alkanoylamino, aroylamino, aralkanoylamino, substituted alkanoylamino, substituted arylamino, substituted aralkanoylamino, thiol, alkylthio, arylthio, aralkylthio, cycloalkylthio, heterocyclothio, alkylthiono, arylthiono, aralkylthiono, alkylsulfonyl, arylsulfonyl, aralkylsulfonyl, sulfonamido (e.g. $SO_2NH_2$), substituted sulfonamido, nitro, cyano, carboxy, carbamyl (e.g. $CONH_2$), substituted carbamyl (e.g. CONH alkyl, CONH aryl, CONH aralkyl or instances where there are two substituents on the nitrogen selected from alkyl, aryl or aralkyl), alkoxycarbonyl, aryl, substituted aryl, guanidino and heterocyclos, such as, indolyl, imidazolyl, furyl, thienyl, thiazolyl, pyrrolidyl, pyridyl, pyrimidyl and the like. Wherein, as noted above, the substituents themselves are further substituted, such further substituents are selected from the group consisting of halogen, alkyl, alkoxy, aryl and aralkyl. The definitions given herein for alkyl and substituted alkyl apply as well to the alkyl portion of alkoxy groups.

The term "alkenyl" refers to optionally substituted unsaturated aliphatic hydrocarbon groups having from one to nine carbons and one or more double bonds. Substituents may include one or more substituent groups as described above for substituted alkyl.

The term "halogen" or "halo" refers to fluorine, chlorine, bromine and iodine.

The term "ring system" refers to an optionally substituted ring system containing one to three rings and at least one carbon to carbon double bond in at least one ring. Exemplary ring systems include, but are not limited to, an aryl or a partially or filly unsaturated heterocyclic ring system, which may be optionally substituted.

The term "aryl" refers to monocyclic or bicyclic aromatic hydrocarbon groups having from 6 to 12 carbon atoms in the ring portion, for example, phenyl, naphthyl, biphenyl and diphenyl groups, each of which may be substituted.

The term "aralkyl" refers to an aryl group bonded to a larger entity through an alkyl group, such as benzyl.

The term "substituted aryl" refers to an aryl group substituted by, for example, one to four substituents such as alkyl; substituted alkyl, halo, trifluoromethyl, trifluoromethoxy, hydroxy, alkoxy, cycloalkyloxy, heterocyclooxy, alkanoyl, alkanoyloxy, amino, alkylamino, dialkylamino, aralkylamino, cycloalkylamino, heterocycloamino, alkanoylamino, thiol, alkylthio, cycloalkylthio, heterocyclothio, ureido, nitro, cyano, carboxy, carboxyalkyl, carbamyl, alkoxycarbonyl, alkylthiono, arylthiono, alkysulfonyl, sulfonamido, aryloxy and the like. The substituent may be further substituted by one or more members selected from the group consisting of halo, hydroxy, alkyl, alkoxy, aryl, substituted alkyl, substituted aryl and aralkyl.

The term "cycloalkyl" refers to optionally substituted saturated cyclic hydrocarbon ring systems, preferably containing 1 to 3 rings and 3 to 7 carbons per ring, which may be further fused with an unsaturated $C_3$–$C_7$ carbocyclic ring. Exemplary groups include cyclopropyl, cyclobutyl, cyclopentyl, cyclohexyl, cycloheptyl, cyclooctyl, cyclodecyl, cyclododecyl, and adamantyl. Exemplary substituents include one or more alkyl groups as described above, or one or more of the groups described above as substituents for alkyl groups.

The terms "heterocycle", "heterocyclic" and "heterocyclo" refer to an optionally substituted, unsaturated, partially saturated, or fully saturated, aromatic or nonaromatic cyclic group, for example, which is a 4 to 7 membered monocyclic, 7 to 11 membered bicyclic, or 10 to 15 membered tricyclic ring system, which has at least one heteroatom in at least one carbon atom-containing ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized and the nitrogen heteroatoms may also optionally be quaternized. The heterocyclic group may be attached at any heteroatom or carbon atom.

Exemplary monocyclic heterocyclic groups include pyrrolidinyl, pyrrolyl, indolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolidinyl, 2-oxazepinyl, azepinyl, 4-piperidonyl, pyridyl, N-oxo-pyridyl, pyrazinyl, pyrimidinyl, pyridazinyl, tetrahydropyranyl, tetrahydrothiopyranyl, tetrahydrothiopyranyl sulfone, morpholinyl, thiomorpholinyl, thiomorpholinyl sulfoxide, thiomorpholinyl sulfone, 1,3-dioxolane and tetrahydro-1,1-dioxothienyl, dioxanyl, isothiazolidinyl, thietanyl, thiiranyl, triazinyl, and triazolyl, and the like.

Exemplary bicyclic heterocyclic groups include benzothiazolyl, benzoxazolyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopyridyl, furopyridinyl (such as furo[2,3-c]pyridinyl, furo[3,1-b]pyridinyl] or furo[2,3-b] pyridinyl), dihydroisoindolyl, dihydroquinazolinyl (such as 3,4-dihydro-4-oxo-quinazolinyl), benzisothiazolyl, benzisoxazolyl, benzodiazinyl, benzofurazanyl, benzothiopyranyl, benzotriazolyl, benzpyrazolyl, dihydrobenzofuryl, dihydrobenzothienyl, dihydrobenzothiopyranyl, dihydrobenzothiopyranyl sulfone, dihydrobenzopyranyl, indolinyl, isochromanyl, isoindolinyl, naphthyridinyl, phthalazinyl, piperonyl, purinyl, pyridopyridyl, quinazolinyl, tetrahydroquinolinyl, thienofuryl, thienopyridyl, thienothienyl, and the like.

Exemplary substituents for the terms "ring system," "heterocycle," "heterocyclic," and "heterocyclo" include one or more substituent groups as described above for substituted alkyl or substituted aryl, and smaller heterocyclos, such as, epoxides, aziridines and the like.

The term "alkanoyl" refers to —C(O)-alkyl.

The term "substituted alkanoyl" refers to —C(O)-substituted alkyl.

The term "heteroatoms" shall include oxygen, sulfur and nitrogen.

The compounds represented by formula II form salts with a variety of organic and inorganic acids. Such salts include those formed with hydrogen chloride, hydrogen bromide, methanesulfonic acid, hydroxyethanesulfonic acid, sulfuric acid, acetic acid, trifluoroacetic acid, maleic acid, benzenesulfonic acid, toluenesulfonic acid and various others as are recognized by those of ordinary skill in the art of pharmaceutical compounding. Such salts are formed by reacting a compound represented by formula II in an equivalent amount of the acid in a medium in which the salt precipitates or in an aqueous medium followed by evaporation.

In addition, zwitterions ("inner salts") can be formed and are included within the term salts as used herein.

The compounds represented by formulae I and II above may exist as multiple optical, geometric, and stereoisomers. While the compounds shown herein are depicted for one optical orientation, included within the present invention are all isomers and mixtures thereof.

Use and Utility

The invention is a process by which compounds represented by formula II above that are microtubule-stabilizing agents are produced. The compounds, and thus the process, are useful in the treatment of a variety of cancers and other proliferative diseases including, but not limited to, the following;

carcinoma, including that of the bladder, breast, colon, kidney, liver, lung, ovary, pancreas, stomach, cervix, thyroid and skin, including squamous cell carcinoma;

hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma and Burketts lymphoma;

hematopoietic tumors of myeloid lineage, including acute and chronic myelogenous leukemias and promyelocytic leukemia;

tumors of mesenchymal origin, including fibrosarcoma and rhabdomyoscarcoma;

other tumors, including melanoma, seminoma, teratocarcinoma, neuroblastoma and glioma;

tumors of the central and peripheral nervous system, including astrocytoma, neuroblastoma, glioma, and schwannomas;

tumors of mesenchymal origin, including fibrosarcoma, rhabdomyoscaroma, and osteosarcoma; and other tumors, including melanoma, xeroderma pigmentosum, keratoacanthoma, seminoma, thyroid follicular cancer and teratocarcinoma.

The compounds produced by the invention as represented by formula II above will also inhibit angiogenesis, thereby affecting the growth of tumors and providing treatment of tumors and tumor-related disorders. Such anti-angiogenesis properties of the compounds represented by formula II will also be useful in the treatment of other conditions responsive to anti-angiogenesis agents including, but not limited to, certain forms of blindness related to retinal vascularization, arthritis, especially inflammatory arthritis, multiple sclerosis, restinosis and psoriasis.

Compounds produced by the invention as represented by formula II will induce or inhibit apoptosis, a physiological cell death process critical for normal development and homeostasis. Alterations of apoptotic pathways contribute to the pathogenesis of a variety of human diseases. Compounds represented by formula II, as modulators of apoptosis, will be useful in the treatment of a variety of human diseases with aberrations in apoptosis including, but not limited to, cancer and precancerous lesions, immune response related diseases, viral infections, degenerative diseases of the musculoskeletal system and kidney disease.

Without wishing to be bound to any mechanism or morphology, the compounds produced by the invention as represented by formula II may also be used to treat conditions other than cancer or other proliferative diseases. Such conditions include, but are not limited to viral infections such as herpesvirus, poxvirus, Epstein-Barr virus, Sindbis virus and adenovirus; autoimmune diseases such as systemic lupus erythematosus, immune mediated glomerulonephritis, rheumatoid arthritis, psoriasis, inflammatory bowel diseases and autoimmune diabetes mellitus; neurodegenerative disorders such as Alzheimer's disease, AIDS-related dementia, Parkinson's disease, amyotrophic lateral sclerosis, retinitis pigmentosa, spinal muscular atrophy and cerebellar degeneration; AIDS; myelodysplastic syndromes; aplastic anemia; ischemic injury associated myocardial infarctions; stroke and reperfusion injury; restenosis; arrhythmia; atherosclerosis; toxin-induced or alcohol induced liver diseases; hematological diseases such as chronic anemia and aplastic anemia; degenerative diseases of the musculoskeletal system such as osteoporosis and arthritis; aspirin-sensitive rhinosinusitis; cystic fibrosis; multiple sclerosis; kidney diseases; and cancer pain.

General Methods of Preparation

The novel open-ring intermediates represented by formula I can be prepared from an epothilone starting material represented by formula III in Scheme 1 wherein Q, Z, and $R^1$ through $R^6$ are as defined above. The epothilone starting materials represented by formula III are known compounds, see, for example, Hofle, G., et al., *Angew. Chem. Int. Ed. Engl.*, Vol. 35, No.13/14, 1567–1569 (1996); WO93/10121 published May 27, 1993; and WO97/19086 published May 29, 1997; Nicolaou, K. C., et al., *Angew Chem. Int. Ed. Engl.*, Vol. 36, No. 19, 2097–2103 (1997); and Su, D.-S., et al., *Angew Chem. Int. Ed. Engl.*, Vol. 36, No. 19, 2093–2097 (1997).

As illustrated in Scheme 1, the epothilone starting material III is reacted with a suitable azide donor agent and a reducing agent in the presence of a phase transfer catalyst and a palladium catalyst under mildly acidic conditions, i.e. a pH not below about 5.5, preferably from pH 6.0 to 6.5, most preferably about 6.5, in a suitable mixed solvent system comprising water and an organic solvent such as THF, DMF and the like. The reaction is conducted at ambient temperature for an extended period, e.g. in excess of twelve hours.

The epothilone starting material for this invention can be any epothilone comprising an epothilone core and side chain as defined herein. Preferably the starting material is a compound represented by formula III in Scheme 1.

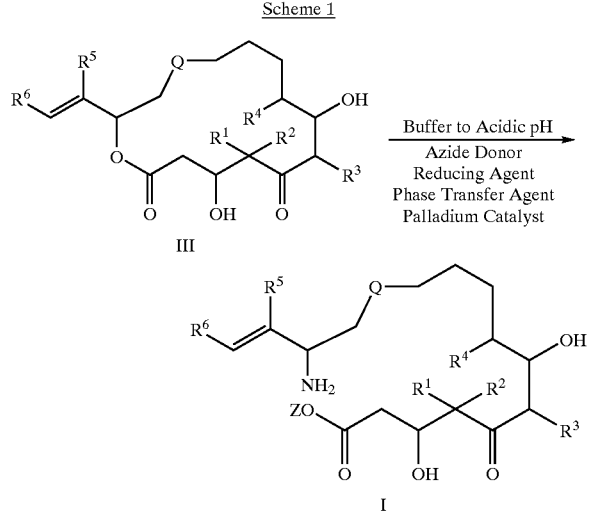

Scheme 1

Suitable azide donor agents for this reaction include metal azides, for example lithium or sodium azide, tetraalkylammonium azides, for example, tetrabutylammonium azide, trialkylsilyl azides, for example trimethylsilyl azide, and the like, Preferred azide donors are sodium azide and tetrabutyl ammonium azide. An especially preferred azide donor is tetrabutylammonium azide.

Suitable reducing agents are trialkylphosphine, triarylphosphine, tri(alkyl/aryl)phosphine, trialkylarsine, triarylarsine, tri(alkyl/aryl)arsine and mixtures thereof Preferred reducing agents are trimethyl phosphine, triethyl phosphine, tributyl phosphine, triphenyl phosphine, and tripropyl phosphine. An especially preferred reducing agent is trimethyl phosphine ($PME_3$).

Suitable phase transfer catalysts or agents may include any quaternary onium salt and their corresponding anions. Suitable phase transfer agents include tetraalkylonium, tetrararylonium, tetraaralkylonium, and any combination of these types of onium substituents. More specifically the phase transfer catalyst may include tetraalkylammonium halides such as tetrabutylammonium chloride or benzyltriethylammonium chloride. An especially preferred phase transfer agent is tetrabutylammonium chloride. The onium substituent may be ammonium, phosphonium, or arsonium. Exemplary anions for these quartenary salts include, but are not limited to, halides, hydroxyl, cyano, phosphate, sulfate and the like. Other suitable phase transfer catalysts or agents are described in Yuri Goldberg, *Phase Transfer Catalysis*, Gordon and Breach Science Publishers, 1992, Chapter 1 and the references cited therein, the full text of which is incorporated herein by reference.

The palladium catalyst for the reaction shown in Scheme 1 may be, for example, palladium acetate, palladium chloride, palladium tetrakis-(triphenyl-phosphine), palladium tetrakis-(triphenylarsine), tris-(dibenzylideneacetone)-dipalladium(0)chloroform adduct ($Pd2(dba)3.CHCl_3$ and the like. A preferred catalyst is tris-(dibenzylideneacetone)- dipalladium(0)chloroform adduct (Pd₂(dba)₃.CHCl₃). Tris-(dibenzylideneacetone)-dipalladium is also a useful catalyst in the reaction illustrated in Scheme 1. The chemistry of the palladium catalysts is known, see for example, I. J. Tsuji, *Palladium Reagents and Catalysts: Innovations in Organic Synthesis*, New York, Wiley and Sons, 1995, the full text of which is incorporated herein by reference.

Suitable buffering agents to maintain the pH within the desired range include a mild acid or acidic salt, such as acetic acid, sodium biphosphate and, preferably, ammonium chloride.

As shown in Scheme 2, epothilone analogs represented by formula II are prepared from the novel open-ring intermediates represented by formula I by macrolactamization utilizing a suitable macrolactamization or coupling agent in a mixed organic solvent system, such as THF/DMF.

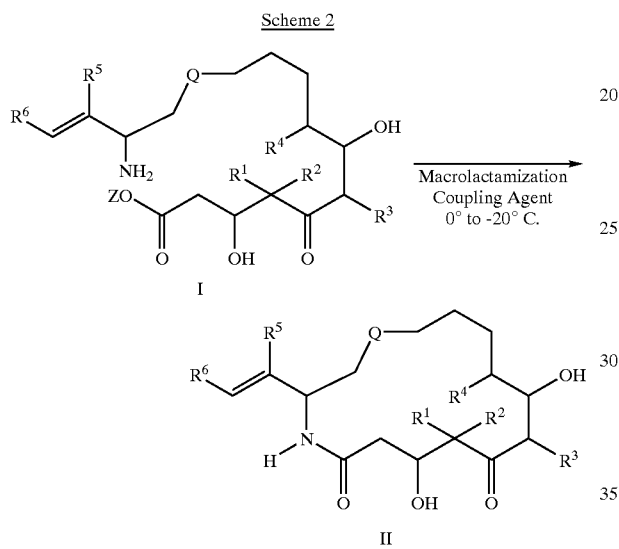

Scheme 2

Macrolactamization agents for the reaction include 1-(3-dimethylaminopropyl)-3-ethylcarbodiimide hydrochloride (EDCI), or EDCI in combination with 1-hydroxy-7-azabenzotriazole (HOAT) or 1-hydroxy-7-benzotriazole hydrate (HOBT), other carbodiimides such as dicyclohexylcarbodiimide and diisopropylcarbodiimide, O-benzotriazol-1-yl-N,N, N',N'-bis(tetramethylene)uronium hexafluorophosphate (HBTu/DMAP), O-(7-azabenzotriazol)-1-yl-N,N,N',N'-bis(tetramethylene) uronium hexafluorophosphate (HATu/DMAP), benzotriazole-1-yloxy-tris(bimethylamino)phosphonium hexafluorophosphate (BOP), N,N-dimethyl-4-aminopyridine (DMAP), K₂CO₃, diisopropylamine, triethylamine and the like. A preferred macrolactamization agent includes 1-(3-dimethylaminopropyl)-3-ethylcarbodiimide hydrochloride (EDCI) in combination with 1-hydroxy-7-benzotriazole (HOBT). Examples of other suitable macrolactamization agents can be found in J. M. Humphrey and A. R. Chamberlin, *Chem. Rev.* 97, 2243–2266, (1997), the full text of which is incorporated herein by reference.

The cyclization reaction as shown in Scheme 2 is carried out in the cold, i.e. a temperature of from about 0° C. to about −20° C., preferably from about −5° C. to −10° C.

The reaction of Scheme 2 is carried out in mildly alkaline conditions with a mild base such as K₂CO₃, triethylamine, diisopropylamine and the like, preferably with K₂CO₃, to inhibit the production of any unwanted by-products.

Scheme 3 below illustrates a preferred embodiment of the invention. The synthesis of the compounds represented by formula II from the starting epothilone material, epothilone B represented by formula III, is sequentially reacted without isolation of the novel intermediate represented by formula I as illustrated.

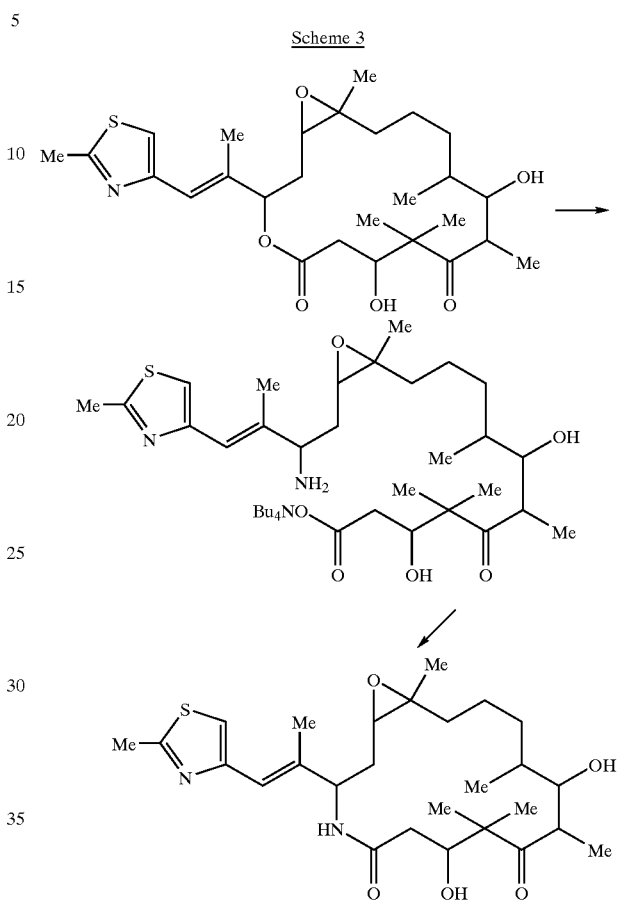

Scheme 3

It has been found in accordance with the present invention that the compounds represented by formula II can be prepared in significantly improved yields in comparison to prior methods. Typically, the instant process produces about a three fold increase in yield.

All references cited herein are incorporated by reference as if set forth at length herein.

The following non-limiting examples serve to illustrate the practice of the invention.

EXAMPLE 1

(βS, εR, ζS, ηS, 2R, 3S)-3-[(2S, 3E)-2-amino-3-methyl-4-(2-methyl-4-thiazol)-3-butenyl]-β, ζ-dihydroxy-γ,γ,ε,η, 2-pentamethyl-δ-oxooxiraneundecanoic Acid, tetrabutylammuonium Salt (1:1)

In a 250 mL round bottom flask there was combined epothilone B (3.87 g), sodium azide (NaN₃) (0.99 g, 2.0 equivalent), tetrabuytlammonium chloride (Bu₄NCl) (2.3 g, 1.1 equivalents), ammonium chloride (NH₄Cl) (0.82 g, 2.0 equivalents) and tetrahydrofuran (THF) (60 mL). The resulting suspension was degassed with argon and there was added thereto water (1.37 g, 10 equivalents, pre-degassed), trimethyl phosphine (PMe₃) (15.2 mL, 1.0M solution in THF, 2.0 equivalents). The reaction temperature of the mixture was equilibrated to 25° C. before the addition of tris-(dibenzylideneacetone)-dipalladium (0)chloroform adduct (Pd₂(dba)₃·CHCl₃) (158 mg, 0.02 equivalents). The resulting solution was magnetically stirred under an argon atmosphere for 19 hours and water (30 mL) and ethyl acetate (EtOAc) (30 mL) were added thereto. The two layers of the resulting mixture were separated and the aqueous layer extracted three times with 25 mL portions of ethyl acetate. The combined ethyl acetate layer was back extracted with three 15 mL portions of water. The resulting combined aqueous layer was saturated with sodium chloride (NaCl) and the pH thereof adjusted to from 6 to 6.5 with sodium phosphate monobasic (NaH₂PO₄). The resulting suspension was extracted with five 25 mL portions of dichloromethane (CH₂Cl₂) and the extracts were combined and dried over sodium sulfate. The suspension was filtered and the filtrate concentrated to provide 5.6 g of the amino acid salt in 96% yield with a HPLC area of 93%.

EXAMPLE 2

[1S-[1R*,3R*(E),7R*,10S*,11R*,12R*,16S*]]-7,11-Dihydroxy-8,8,10,12,16-pentamethyl-3-[1-methyl-2-(2-methyl-4-thiazolyl)ethenyl]-4-aza-17-oxabicyclo[14.1.0]heptadecane-5,9-dione

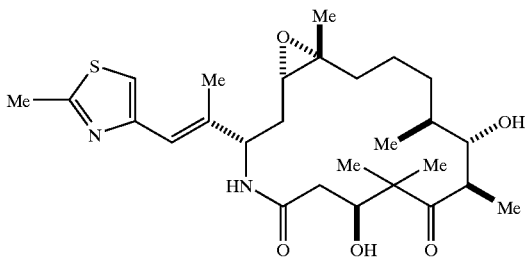

The amino acid salt formed in Example 1 (4.18 g) was dissolved in a one to one mixture of tetrahydrofuran (THF) and N,N-dimethylformamide (DMF) (270 mL) and the resulting solution was cooled to −5° C. There was added potassium carbonate(K₂CO₃) (0.75 g, 1.0 equivalent) and the mixture stirred for five minutes before the addition of 1-hydroxy-7-benzotriazole hydrate (HOBt) (0.88 g, 1.2 equivalents) and 1-(3-dimethylaminopropyl)-3-ethylcarbodiimide hydrochloride (EDCI) (2.09 g, 2.0 equivalents). The resulting mixture was stirred at −5° C. for two hours, 0° C. for eight hours and 10° C. for two hours. There was then added ethyl acetate (ETOAc) (500 mL) and the resulting organic layer was washed with five 120 mL portions of water. The combined aqueous layer was washed three times with 100 mL portions of ethyl acetate. The combined organic layer was back extracted with three portions (100 mL each) of water, 100 mL of brine, and dried over magnesium sulfate) (MgSO₄). Filtration followed by concentration provided 2.50 g of crude [1S-1R*,3R*(E),7R*,10S*,-11R*,12R*,16S*]]-7,11-Dihydroxy-8,8,10,12,16-pentamethyl-3-[1-methyl-2-(2-methyl-4-thiazolyl) ethenyl]-4-aza-17-oxabicyclo[14.1.0]heptadecane-5,9-dione as a white solid in 92.7% yield with an HPLC AP of 94.75. The product was passed through a pad of silica gel by means of a solution of ethyl acetate/cyclohexane/triethyl amine (Et₃N) (3/7/0.04) and crystallized from a mixture of ethyl acetate and cyclohexane to give 1.6 g of purified product in 56% yield from epothilone B with a HPLC area of 99.0%.

EXAMPLE 3

[1S-[1R*,3R*(E),7R*,10S*,11R*,12R*,16S*]]-7,11-Dihydroxy-8,8,10,12,16-pentamethyl-3-[1-methyl-2-(2-methyl-4-thiazolyl)ethenyl]-4-aza-17-oxabicyclo[14.1.0]heptadecane-5,9-dione

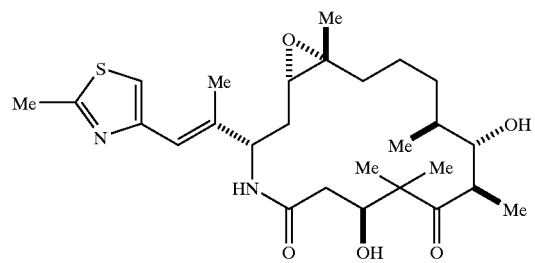

To a jacketed 125 mL round bottom flask, fitted with a mechanical stirrer, there was combined epothilone-B (5.08 g), tetrabutyammonium azide (Bu₄NN₃) (3.55 g, 1.25 equivalents), ammonium chloride (1.07 g, 2 eq), water (1.8 ml, 10 equivalents), tetrahydrofuran (THF) (15 ml), and N,N-dimethylformamide (DMF) (15 ml). The mixture was inerted by sparging nitrogen subsurface for 15 minutes. In a second flask was charged tetrahydrofuran (70 ml), followed by trimethylphosphine (PMe₃) (1.56 ml, 1.5 equivalents), then tris(dibenzilidineacetone)-dipalladium(0)-chloroform adduct (Pd₂(dba)₃·CHCl₃)(0.259 g, 0.025 equivalents). The catalyst mixture was stirred for 20 minutes at ambient temperature, then added to the epothilone-B mixture. The combined mixture was stirred for 4.5 hours at 30° C. The completed reaction mixture was then filtered to remove solid ammonium chloride (NH₄Cl). The filtrate contained (βS, εR, ζS, ηS, 2R, 3S)-3-[(2S, 3E)-2-amino-3-methyl-4-(2-methyl-4-thiazolyl)-3-butenyl]-β, ζ-dihydroxy-γ,γ,ε,η,2-pentamethyl-δ-oxooxxiraneundecanoic acid, tetrabutylammonium salt (1:1) with a HPLC area of 94.1%.

In a 500 mL flask there was combined 1-[3-(dimethylamino)propyl]-3-ethylcarbodiimide hydrochloride (EDCI) (3.82 g, 2 equivalents), 1-hydroxy-7-benzotriazole hydrate (HOBt) (1.68 g, 1.1 equivalents), potassium carbonate (1.38 g, 1 equivalent), N,N-dimethylformamide (DMF) (40 ml) and tetrahydrofuran (THF) (160 ml). The mixture was warmed to 35° C. and the filtrate from above was added thereto, dropwise over a period of three hours. This mixture was then stirred for an additional 1 hour at 35° C. Vacuum distillation was then applied to the reaction mixture to reduce the volume thereof to about 80 mL. The resulting solution was partitioned between 100 mL of ethyl acetate and 100 mL of water. The aqueous layer was then back-extracted with 100 ml ethyl acetate. The combined organic layers were extracted with 50 ml water and then 20 mL brine. The resulting product solution was filtered through a Zeta Plus® pad and then stripped to an oil. The crude oil was chromatographed on silica gel 60 (35 ml silica per gram of theoretical product) with an eluent comprised of 88% dichloromethane (CH₂Cl₂), 10% ethyl acetate (EtOAc) and 2% triethylamine (Et₃N). The fractions were analyzed by HPLC, the purest of which were combined and stripped to give the purified solid. The resulting solid was slurried in ethyl acetate (32 ml) for 40 minutes at 75° C., then cyclohexane (C₆H₁₂) (16 ml) was added, and the mixture cooled to 5° C. The purified solid was collected on filter paper, washed with cold ethyl acetate/cyclohexane, and dried. The yield was 1.72 g (38% yield) of the white solid product, [1S-[1R*,3R*(E),7R*,10S*,11R*,12R*,16S*]]-7,11-dihydroxy-8,8,10,12,16-pentamethyl-3-[1-methyl-2-(2-methyl-4-thiazolyl)ethenyl]-4-aza-17-oxabicyclo[14.1.0]heptadecane-5,9-dione, with a HPLC area of 99.2%.

EXAMPLE 4

[1S-[1R*,3R*(E),7R*,10S*,11R*,12R*,16S*]]-7,1-Dihydroxy-8,8,10,12,16-pentamethyl-3-[1-methyl-2-(2-methyl-4-thiazolyl)ethenyl]-4-aza-17-oxabicyclo [14.1.0]heptadecane-5,9-dione

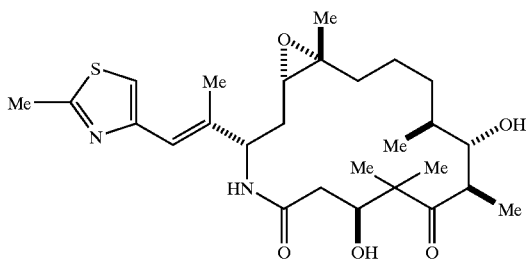

In another embodiment of the invention the title compound can be prepared in a single reaction vessel without isolating the intermediate salt (represented as formula I) as follows. #

In a 25 mL round bottom flask is combined epothilone B (3.87 g), sodium azide (NaN₃) (0.99 g, 2.0 equivalents), tetrabutylammonium chloride (Bu₄NCl) (2.3 g, 1.1 equivalents), ammonium chloride (NH₄Cl) (0.82 g, 2.0 equivalents) and tetrahydrofuran (THF) (60 mL). The resulting suspension is degassed with argon and there is added thereto water (1.37 g, 10 equivalents, pre-degassed), and trimethylphosphine (PMe₃) (15.2 mL, 1.0M solution in THF, 2.0 equivalents). The reaction temperature of the mixture is equilibrated to 25° C. before the addition of tris(dibenzilidineacetone)-dipalladium(0)-chloroform adduct (Pd₂(dba)₃·CHCl₃) (158 mg, 0.02 equivalents). The resulting solution is stirred under an argon atmosphere for seventeen hours. The temperature of the reaction solution is cooled to -5° C. There is added potassium carbonate (K₂CO₃) (0.75 g, 1.0 equivalent) and the mixture is stirred for five minutes before the addition of 1-hydroxy-7-benzotriazole hydrate (HOBt) (0.88 g, 1.2 equivalents) and 1-[3-(dimethylamino)propyl]-3-ethylcarbodiimide hydrochloride (EDCI) (2.09 g, 2.0 equivalents). Then resulting mixture is stirred at -5° C. for two hours, 0° C. for eight hours and 10° C. for two hours. Ethyl acetate (500 mL) is added and the resulting organic layer is washed with five 120 mL portions of water. The combined aqueous layer is back extracted three times with 100 mL portions of ethyl acetate. The combined organic layers are then washed with 100 mL of brine and dried over magnesium sulfate (MgSO₄). Filtration followed by concentration provides about 2.50 g of the named product as a white solid. The product is passed through a pad of silica gel by means of a solution of ethyl acetate/cyclohexane/triethylamine (Et₃N) (3/7/0.04) and crystallized from a mixture of ethyl acetate and cyclohexane to give about 1.6 g of purified product.

EXAMPLE 5

Tetrabutylammonium Azide (Bu₄NN₃)

To a 50 mL round bottom flask, fitted with a magnetic stirring bar, there was combined tetrabutylammonium chloride (Bu₄NCl.H₂O) (7.78 g, 1.4 equivalents) sodium azide (1.82 g 1.4 equivalents) in DMF 14 mL. The mixture was stirred for 72 h at 20–21° C. The reaction was diluted with THF (28 mL) and the solids were filtered off and washed with THF (12 mL).

EXAMPLE 6

Tetrabutylammonium Azide (Bu₄NN₃)

To a 50 mL round bottom flask, fitted with a magnetic stirring bar, there was combined tetrabutylammonium chloride (Bu₄NCl.H₂O) (8.7 g, 1.4 equivalents) sodium azide (2.03 g 1.4 equivalents) in DMF 14 mL. The mixture was stirred for 7 h at 30° C. h. The reaction was diluted with THF (28 mL) and the solids were filtered off and washed with THF (12 mL).

EXAMPLE 7

[1S-[1R*,3R*(E),7R*,10S*,11R*,12R*,16S*]]-7,11-Dihydroxy-8,8,10,12,16-pentamethyl-3-[1-methyl-2-(2-methyl-4-thiazolyl)ethenyl]-4-aza-17-oxabicyclo [14.1.0]heptadecane-5,9-dione

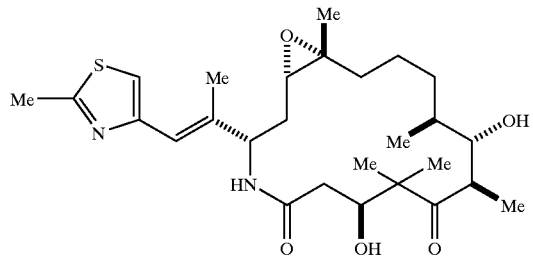

To a 100 mL round bottom flask, fitted with a mechanical stirrer, there was combined epothilone-B (10.15 g), solution of tetrabutylammonium azide (Bu₄NN₃) (56 ml, 1.25 equivalents) in DMF and THF, ammonium chloride (2.14 g, 2 eq), water (3.6 ml, 10 equivalents), and N,N-dimethylformamide (DMF) (6 ml). The mixture was inerted by sparging nitrogen subsurface for 30 minutes. In a second flask was charged tetrahydrofuran (40 ml), followed by trimethylphosphine (PMe₃) (3 ml, 1.5 equivalents), then tris(dibenzilidineacetone)-dipalladium(0)-chloroform adduct (Pd₂(dba)₃·CHCl₃)(0.345 g, 0.017 equivalents). The catalyst mixture was stirred for 20 minutes at ambient temperature, then added to the epothilone-B mixture. The combined mixture was stirred for 18 hours at 31–35° C. The completed reaction mixture was then filtered to remove solid ammonium chloride (NH₄Cl). The filtrate contained (βS, εR, ζS, ηS, 2R, 3S)-3-[(2S, 3E)-2-amino-3-methyl-4-(2-methyl-4thiazolyl)-3-butenyl]β,ζ-dihydroxy-γ,γ,ε,η, 2-pentamethyl-δ-oxooxirane-undecanoic acid, tetrabutylammonium salt (1:1).

In a 250 mL flask there was combined 1-[3-(dimethylamino)propyl]-3-ethylcarbodiimide hydrochloride (EDCI) (7.64 g, 2 equivalents), 1-hydroxy-7-benzotriazole hydrate (HOBt) (3.06 g, 1 equivalent), potassium carbonate (1.41 g, 0.5 equivalent), N,N-dimethylformamide (DMF) (40 ml) and tetrahydrofuran (THF) (24 ml). The mixture was warmed to 35° C. and the filtrate from above was added thereto, slowly over a period of four hours. The resulting solution was then partitioned between 80 mL of ethyl acetate and 210 mL of water. The aqueous layer was then back-extracted with 2×80 ml ethyl acetate. The combined organic layers were extracted with 120 ml water and dried over sodium sulfate. The resulting product solution was stirred over Darco KRB (1 g) for 2 h. The crude solution was filtered through a pad of florisil (3 g of florisil per gram of input). The column was rinsed with ethyl acetate (60 mL). The combined filtrate was concentrated under vacuo to a final volume of ~100 mL below 30° C. The resulting slurry in ethyl acetate was heated for 30 minutes at 71° C., then heptane ($C_7H_{16}$) (50 ml) was added, and the mixture cooled to 21° C. The purified solid was collected on filter paper, washed with ethyl acetate/heptane, and dried. The yield was 4.4 g (44% yield) of the white solid product, [1S-[1R*,3R*(E),7R*,10S*,11R*,12R*,16S*]]-7,11-dihydroxy-8,8,10,12,16-pentamethyl-3-[1-methyl-2-(2-methyl-4-thiazolyl)ethenyl]-4-aza-17-oxabicyclo[14.1.0]heptadecane-5,9-dione, with a HPLC area of 98.3%.

EXAMPLE 8

[1S-[1R*,3R*(E),7R*,10S*,11R*,12R*,16S*]]-7,11-Dihydroxy-8,8,10,12,16-pentamethyl-3-[1-methyl-2-(2-methyl-4-thiazolyl)ethenyl]-4-aza-17-oxabicyclo [14.1.0]heptadecane-5,9-dione

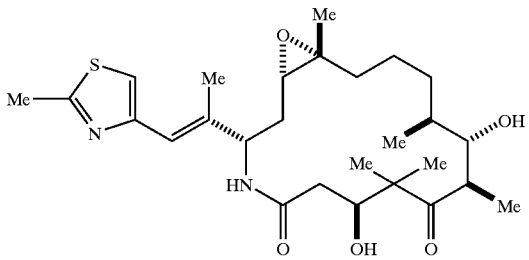

To a 100 mL round bottom flask, fitted with a mechanical stirrer, there was combined epothilone-B (5.1 g), solution of tetrabutylammonium azide ($Bu_4NN_3$) (29 ml, 1.30 equivalents) in DMF and THF, ammonium chloride (1.07 g, 2 eq), water (1.8 ml, 10 equivalents), and N,N-dimethylformamide (DMF) (3 ml). The mixture was inerted by sparging nitrogen subsurface for 30 minutes. In a second flask was charged tetrahydrofuran (20 ml), followed by trimethylphosphine ($PMe_3$) (1.5 ml, 1.5 equivalents), then tris(dibenzilidineacetone)-dipalladium(0)-chloroform adduct ($Pd_2(dba)_3 \cdot CHCl_3$)(0.175 g, 0.017 equivalents). The catalyst mixture was stirred for 20 minutes at ambient temperature, then added to the epothilone-B mixture. The combined mixture was stirred for 18 hours at 31–35° C. The completed reaction mixture was then filtered to remove solid ammonium chloride ($NH_4Cl$), followed by a zeta pad (R53SP or R51SP) filtration. The filtrate contained (βS, εR, ζS, ηS, 2R, 3S)-3-[(2S, 3E)-2-amino-3-methyl-4-(2-methyl-4-thiazolyl)-3-butenyl]-β, ζ-dihydroxy-γ,γ,ε,η,2-pentamethyl-δ-oxooxxiraneundecanoic acid, tetrabutylammonium salt (1:1).

In a 100 mL flask there was combined 1-[3-(dimethylamino)propyl]-3-ethylcarbodiimide hydrochloride (EDCI) (3.9 g, 2 equivalents), 1-hydroxy-7-benzotriazole hydrate (HOBt) (1.52 g, 1 equivalent), potassium carbonate (0.67 g, 0.5 equivalent), N,N-dimethylformamide (DMF) (20 ml) and tetrahydrofuran (THF) (12 ml). The mixture was warmed to 35° C. and the filtrate from above was added thereto, slowly over a period of four hours. The resulting solution was then partitioned between 25 mL of ethyl acetate and 100 mL of water. The aqueous layer was then back-extracted with 2×25 ml ethyl acetate. The combined organic layers were extracted with 60 ml water. The resulting product solution was filtered through a zeta pad (R53SP or R51SP). The crude solution was diluted with 1 part of cyclohexane and 1%v/v of triethylamine was added. This solution was filtered through a pad of silica gel (5 g of florisil per gram of input). The column was rinsed with 2:1 ethyl acetate:cyclohexane (400 mL) containing 1% v/v triethylamine. After discarding the first 100 ml, the filtrate was concentrated under vacuo to a final volume of ~50 mL below 30° C. Cyclohexane (20 to 30 mL) was added and the resulting slurry was heated for 30 minutes at 71° C. Finally the mixture was cooled to 21° C. The purified solid was collected on filter paper, washed with ethyl acetate/cyclohexane, and dried. The yield was 5.1 g (51% yield) of the white solid product, [1S-[1R*,3R*(E),7R*,10S*,11R*,12R*,16S*]]-7,11-dihydroxy-8,8,10,12,16-pentamethyl-3-[1-methyl-2-(2-methyl-4-thiazolyl)ethenyl]-4-aza-17-oxabicyclo[14.1.0]heptadecane-5,9-dione, with a HPLC area of 99.2%.

We claim:

1. A compound represented by the formula

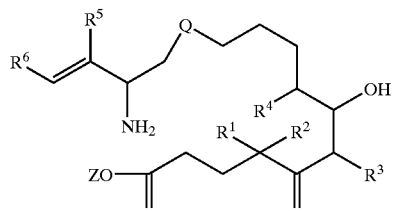

I wherein:
Q is selected from the group consisting of

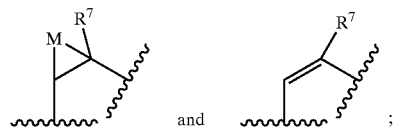

M is selected from the group consisting of oxygen, sulfur, $NR^8$, and $CR^9R^{10}$;
Z is selected from the group consisting of

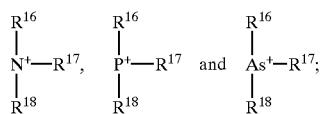

$R^1$-$R^5$, $R^7$, and $R^{11}$-$R^{15}$ are selected from the group consisting of hydrogen, alkyl, substituted alkyl, aryl, substituted aryl and heterocyclo, and wherein $R^1$ and $R^2$ are alkyl, they can be joined to form a cycloalkyl;

$R^6$ is selected from the group consisting of hydrogen, alkyl, substituted alkyl, aryl, substituted aryl, cycloalkyl, heterocyclo and substituted heterocyclo;

$R^8$ is selected from the group consisting of hydrogen, alkyl, substituted alkyl, $R^{11}C=O$, $R^{12}OC=O$ and $R^{13}SO_2$;

$R^9$ and $R^{10}$ are selected from the group consisting of hydrogen, halogen, alkyl, substituted alkyl, aryl, heterocyclo, hydroxy, $R^{14}C=O$, and $R^{15}OC=O$;

$R^{16}$, $R^{17}$, and $R^{18}$ are independently selected from the group consisting of alkyl, aryl, and aralkyl;

and any salts, solvates, or hydrates thereof.

2. A compound in accordance with claim 1 wherein said compound has the formula

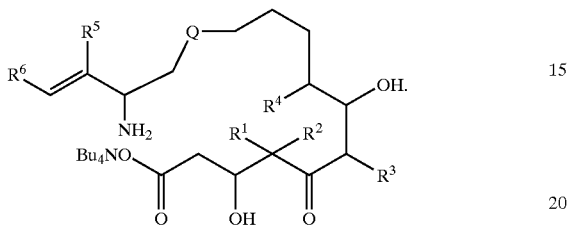

3. A compound in accordance with claim 2 wherein said compound has the structure

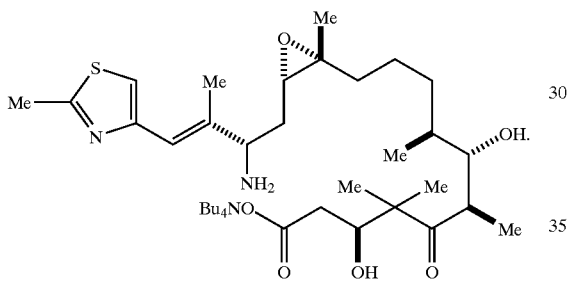

4. A process for preparing a compound represented by the formula

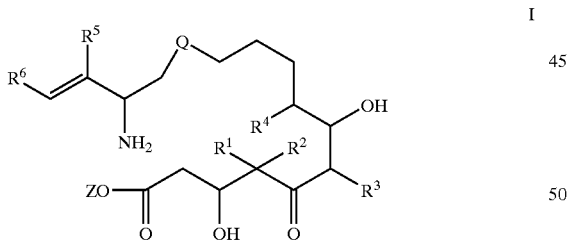

I wherein:

Q is selected from the group consisting of

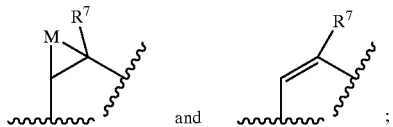

M is selected from the group consisting of oxygen, sulfur, $NR^8$, and $CR^9R^{10}$;

Z is selected from the group consisting of

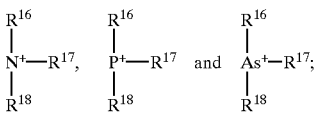

$R^1$–$R^5$, $R^7$, and $R^{11}$–$R^{15}$ are selected from the group consisting of hydrogen, alkyl, substituted alkyl, aryl, substituted aryl and heterocycle, and wherein $R^1$ and $R^2$ are alkyl, they can be joined to form a cycloalkyl;

$R^6$ is selected from the group consisting of hydrogen, alkyl, substituted alkyl, aryl, substituted aryl, cycloalkyl, heterocyclo and substituted heterocyclo;

$R^8$ is selected from the group consisting of hydrogen, alkyl, substituted alkyl, $R^{11}C=O$, $R^{12}OC=O$ and $R^{13}SO_2$;

$R^9$ and $R^{10}$ are selected from the group consisting of hydrogen, halogen, alkyl, substituted alkyl, aryl, heterocyclo, hydroxy, $R^{14}C=O$, and $R^{15}OC=O$;

$R^{16}$, $R^{17}$, and $R^{18}$ are independently selected from the group consisting of alkyl, aryl, and aralkyl;

comprising reacting an epothilone starting material represented by the formula

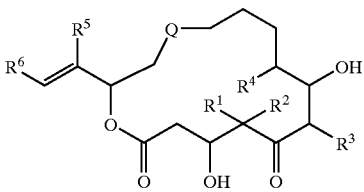

wherein Q, and $R^1$ through $R^6$ are as defined above with an azide donor agent and a reducing agent in the presence of a phase transfer catalyst and a palladium catalyst.

5. A process in accordance with claim 4 for preparing a compound represented by the formula

IV

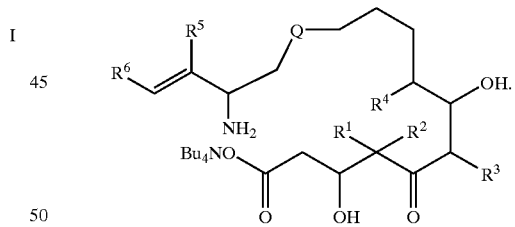

6. A process in accordance with claim 5, wherein said epothilone starting material is epothilone B, and said compound of formula IV is represented by the structure

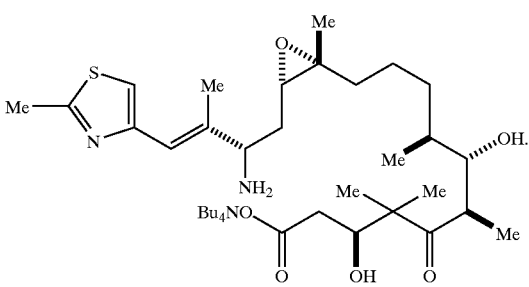

7. A process for preparing a compound represented by the formula

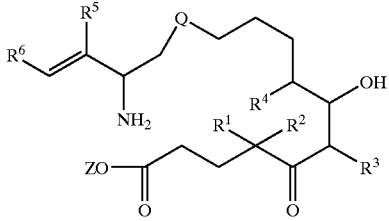

I wherein:

Q is selected from the group consisting of

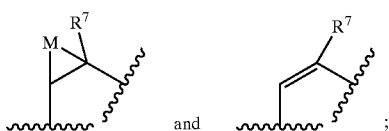

M is selected from the group consisting of oxygen, sulfur, $NR^8$, and $CR^9R^{10}$;
Z is selected from the group consisting of

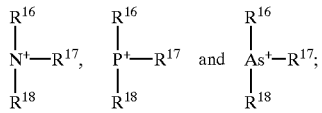

$R^1$–$R^5$, $R^7$, and $R^{11}$–$R^{15}$ are selected from the group consisting of hydrogen, alkyl, substituted alkyl, aryl, substituted aryl and heterocyclo, and wherein $R^1$ and $R^2$ are alkyl, they can be joined to form a cycloalkyl;
$R^6$ is selected from the group consisting of hydrogen, alkyl, substituted alkyl, aryl, substituted aryl, cycloalkyl, heterocyclo and substituted heterocyclo;
$R^8$ is selected from the group consisting of hydrogen, alkyl, substituted alkyl, $R^{11}C=O$, $R^{12}OC=O$ and $R^{13}SO_2$;
$R^9$ and $R^{10}$ are selected from the group consisting of hydrogen, halogen, alkyl, substituted alkyl, aryl, heterocyclo, hydroxy, $R^{14}C=O$, and $R^{15}OC=O$;
$R^{16}$, $R^{17}$, and $R^{18}$ are independently selected from the group consisting of alkyl, aryl, and aralkyl;
comprising reacting an epothilone starting material represented by the formula

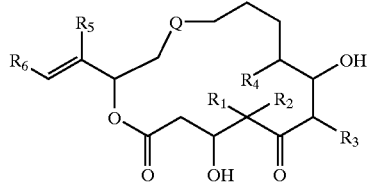

III wherein Q, and $R^1$ through $R^6$ are as defined above with an azide donor agent and a buffering agent in the presence of a palladium catalyst and a reducing agent.

8. A process in accordance with claim 7 for preparing a compound represented by the formula

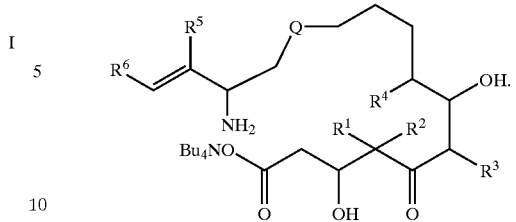

IV

9. A process in accordance with claim 8, wherein said epothilone starting material is epothilone B, and said compound of formula IV is represented by the structure

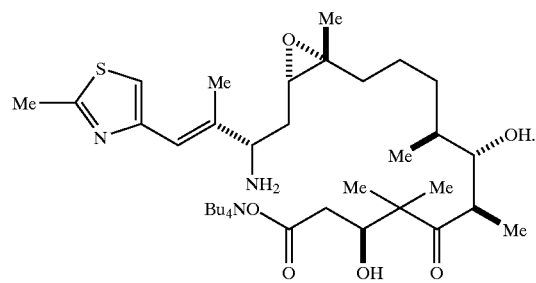

10. A process in accordance with claim 7, wherein said azide donor is tetrabutylammonium azide.

11. A process for the preparation of an epothilone represented by the formula

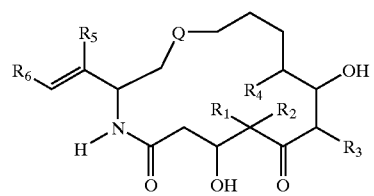

II wherein:

Q is selected from the group consisting of

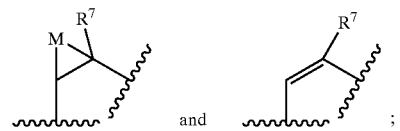

M is selected from the group consisting of oxygen, sulfur, $NR^8$, and $CR^9R^{10}$;
$R^1$–$R^5$, $R^7$, and $R^{11}$–$R^{15}$ are selected from the group consisting of hydrogen, alkyl, substituted alkyl, aryl, substituted aryl and heterocyclo, and wherein $R^1$ and $R^2$ are alkyl, they can be joined to form a cycloalkyl;
$R^6$ is selected from the group consisting of hydrogen, alkyl, substituted alkyl, aryl, substituted aryl, cycloalkyl, heterocyclo and substituted heterocyclo;
$R^8$ is selected from the group consisting of hydrogen, alkyl, substituted alkyl, $R^{11}C=O$, $R^{12}OC=O$ and $R^{13}SO_2$;
$R^9$ and $R^{10}$ are selected from the group consisting of hydrogen, halogen, alkyl, substituted alkyl, aryl, heterocyclo, hydroxy, $R^{14}C=O$, and $R^{15}OC=O$;

which comprises carrying out a macrolactamization reaction of an intermediate compound represented by the formula

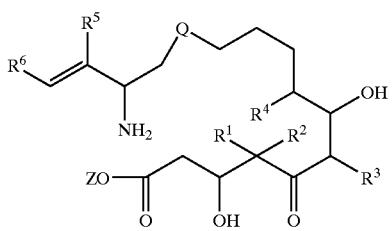

I wherein

Q, and $R^1$ though $R^6$ are as defined above;
Z is selected from the group consisting of

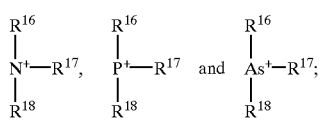

$R^{16}, R^{17}, R^{18}$ are independently selected from the group consisting of alkyl, aryl, and aralkyl;

in the presence of a suitable coupling agent for such reaction.

12. A process in accordance with claim 11 wherein said intermediate is represented by the formula

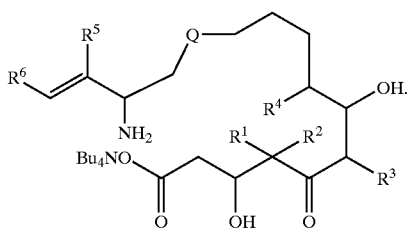

I

13. A process in accordance with claim 12 wherein said epothilone represented by formula II has the structure

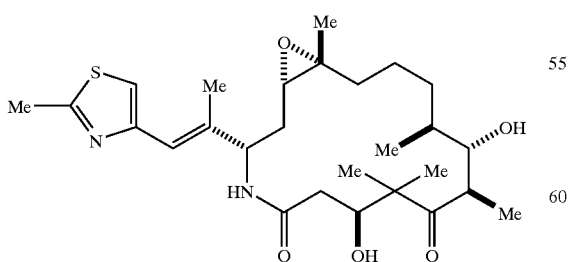

and said macrolactamization reaction is carried out on an intermediate compound represented by the structure

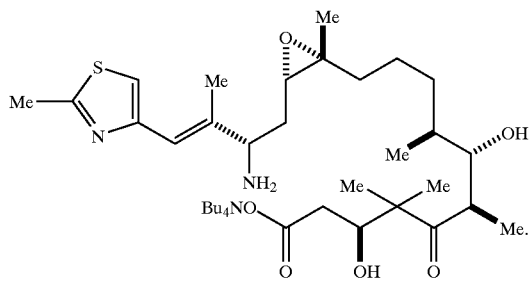

14. A process in accordance with claim 11 wherein said coupling agent comprises 1-(3-dimethylaminopropyl)-3-ethylcarbodiimide hydrochloride and 1-hydroxy-7-benzotriazole hydrate.

15. A process for the preparation of an epothilone represented by the formula

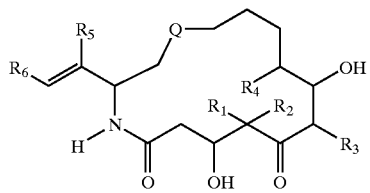

II wherein:

Q is selected from the group consisting of

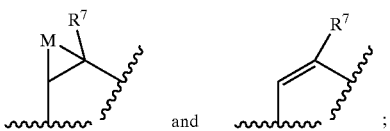

M is selected from the group consisting of oxygen, sulfur, $NR^8$, and $CR^9R^{10}$;
$R^1$–$R^5$, $R^7$, and $R^{11}$–$R^{15}$ are selected from the group consisting of hydrogen, alkyl, substituted alkyl, aryl, substituted aryl and heterocyclo, and wherein $R^1$ and $R^2$ are alkyl, they can be joined to form a cycloalkyl;
$R^6$ is selected from the group consisting of hydrogen, alkyl, substituted alkyl, aryl, substituted aryl, cycloalkyl, heterocyclo and substituted heterocyclo;
$R^8$ is selected from the group consisting of hydrogen, alkyl, substituted alkyl, $R^{11}C=O$, $R^{12}OC=O$ and $R^{13}SO_2$;
$R^9$ and $R^{10}$ are selected from the group consisting of hydrogen, halogen, alkyl, substituted alkyl, aryl, heterocyclo, hydroxy, $R^{14}C=O$, and $R^{15}OC=O$;

comprising reacting an epothilone starting material represented by the formula

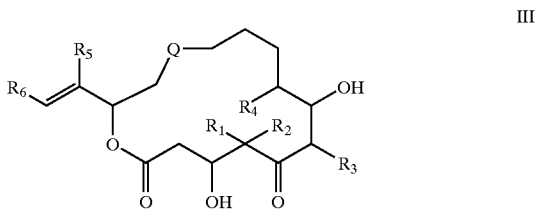

III wherein Q, and $R^1$ through $R^6$ are as defined above, with an azide donor agent and a reducing agent in the presence of a phase transfer catalyst and a palladium catalyst to form an intermediate compound represented by the formula

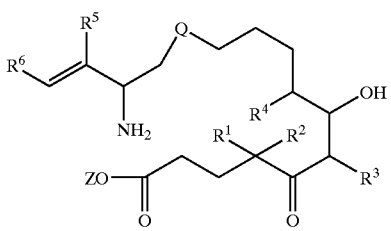

wherein:

Q, and $R^1$ through $R^6$ are as defined above;

Z is selected from the group consisting of

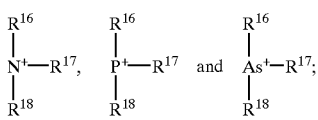

$R^{16}$, $R^{17}$, and $R^{18}$ are independently selected from the group consisting of alkyl, aryl, and aralkyl;

and carrying out a macrolactamization reaction on said intermediate compound in the presence of a suitable coupling agent for such reaction.

16. A process in accordance with claim 15 wherein said intermediate is represented by the formula

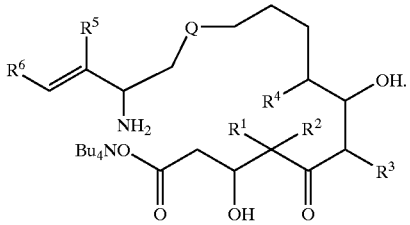

17. A process in accordance with claim 16 wherein said epothilone starting material is epothilone B, said intermediate compound represented by formula I has the structure

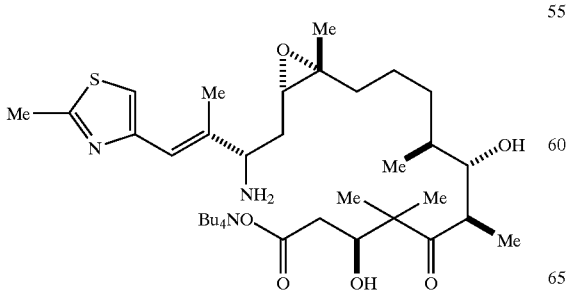

and said epothilone represented by formula II has the structure

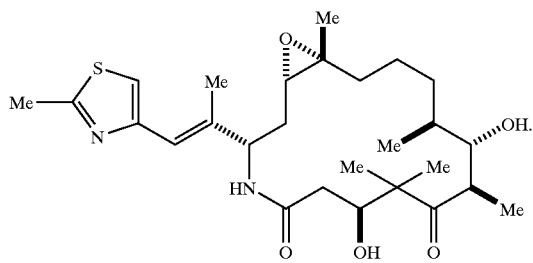

18. A process for the preparation of an epothilone represented by the formula

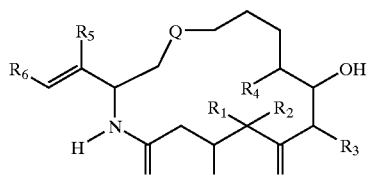

wherein:

Q is selected from the group consisting of

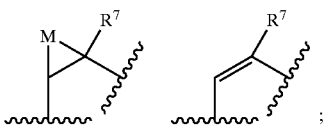

M is selected from the group consisting of oxygen, sulfur, $NR^8$, and $CR^9R^{10}$;

$R^1$–$R^5$, $R^7$, and $R^{11}$–$R^{15}$ are selected from the group consisting of hydrogen, alkyl, substituted alkyl, aryl, substituted aryl and heterocyclo, and wherein $R^1$ and $R^2$ are alkyl, they can be joined to form a cycloalkyl;

$R^6$ is selected from the group consisting of hydrogen, alkyl, substituted alkyl, aryl, substituted aryl, cycloalkyl, heterocyclo and substituted heterocyclo;

$R^8$ is selected from the group consisting of hydrogen, alkyl, substituted alkyl, $R^{11}C=O$, $R^{12}OC=O$ and $R^{13}SO_2$;

$R^9$ and $R^{10}$ are selected from the group consisting of hydrogen, halogen, alkyl, substituted alkyl, aryl, heterocyclo, hydroxy, $R^{14}C=O$, and $R^{15}OC=O$;

comprising reacting an epothilone starting material represented by the formula

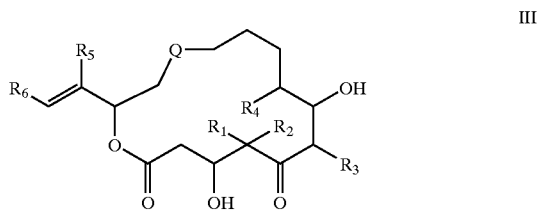

wherein Q, and $R^1$ through $R^6$ are as defined above, with an azide donor agent and a buffering agent in the presence of a palladium catalyst and a reducing agent to form an intermediate compound represented by the formula

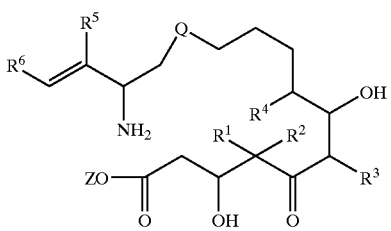

I wherein:

Q, and $R^1$ through $R^6$ are as defined above;

Z is selected from the group consisting of

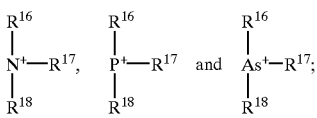

$R^{16}$, $R^{17}$, and $R^{18}$ are independently selected from the group consisting of alkyl, aryl, and aralkyl;

and carrying out a macrolactamization reaction on said intermediate compound in the presence of a suitable coupling agent for such reaction.

19. A process in accordance with claim 18 wherein said intermediate is represented by the formula

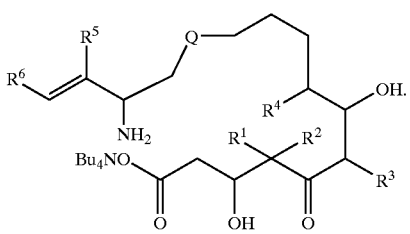

IV

20. A process in accordance with claim 19 wherein said epothilone starting material is epothilone B, said intermediate compound represented by formula IV has the structure

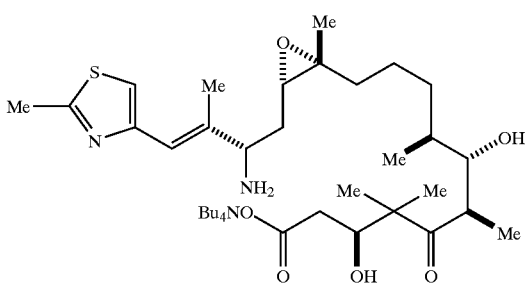

and said epothilone represented by formula II has the structure

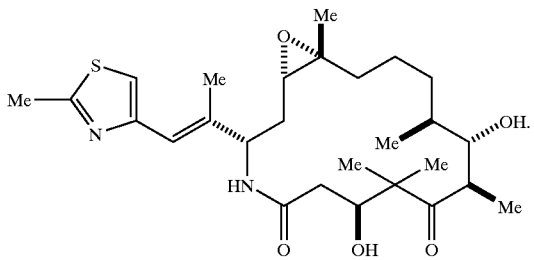

21. A process in accordance with claim 15 wherein said azide donor agent is selected from the group consisting of lithium azide, sodium azide, tetraalkyl-ammonium azide and trialkylsilyl azide, said reducing agent is selected from the group consisting of a trialkylphosphine, triarylphosphine, trialkylarsine, triarylarsine, and mixtures thereof, said phase transfer catalyst is selected from the group consisting of tetraalkylonium, tetraarylonium, tetraaralkylonium salts and mixtures thereof, said palladium catalyst is selected from the group consisting of palladium acetate, palladium chloride, palladium tetrakis-(triphenylphosphine), palladium tetrakris-(triphenylarsine) and tris-(dibenzylideneacetone)-dipalladium(0)chloroform adduct.

22. A process in accordance with claim 21 wherein the azide donor agent is sodium azide, the reducing agent is trimethylphosphine, the phase transfer catalyst is tetrabutylammonium chloride, and the palladium catalyst is tris-(dibenzylideneacetone)-dipalladium(0)chlorofrom adduct.

23. A process in accordance with claim 15 wherein said macrolactamization coupling agent comprises one or more members selected from the group consisting of 1-(3-dimethylaminopropyl)-3-ethylcarbodiimide hydrochloride, 1-(3-dimethylaminopropyl)-3-ethylcarbodiimide hydrochloride and 1-hydroxy-7-benzotriazole hydrate, 1-(3-dimethylaminopropyl)-3-ethylcarbodiimide hydrochloride and 1-hydroxy-7-azabenzotriazole hydrate, dicyclohexylcarbodiimide, diisopropylcarbodiimide, diphenylphosphoryl azide, O-benzotriazol-1-yl-N,N,N',N'-bis(tetramethylene)uronium hexafluorophosphate, O-(7-azabenzotriazol)-1-yl-N,N,N',N'-bis(tetramethylene) uronium hexafluorophosphate, benzotriazol-1-yloxy-tris(bimethylamino)phosphonium hexafluorophosphate, N,N-dimethyl-4-aminopyridine, $K_2CO_3$, diisopropylamine, and triethylamine.

24. A process in accordance with claim 23 where said coupling agent is 1-(3-dimethylaminopropyl)-3-ethylcarbodiimide hydrochloride and 1-hydroxy-7-benzotriazole hydrate.

25. A process in accordance with claim 18 wherein said azide donor agent is selected from the group consisting of lithium azide, sodium azide, tetraalkyl-ammonium azide and trialkylsilyl azide, said buffering agent is selected from the group consisting of mild acids and acidic salts, said palladium catalyst is selected from the group consisting of palladium acetate, palladium chloride, palladium tetrakis-(triphenylphosphine), palladium tetrakris-(triphenylarsine) and tris-(dibenzylideneacetone)-dipalladium(0)chloroform adduct, and said reducing agent is selected from the group consisting of a trialkylphosphine, triarylphosphine, trialkylarsine, triarylarsine, and mixtures thereof.

26. A process in accordance with claim 25 wherein the azide donor agent is tetrabutylammonium azide, the buffering agent is ammonium chloride, the palladium catalyst is tris-(dibenzylideneacetone)-dipalladium(0)chloroform adduct, and the reducing agent is trimethylphosphine.

27. A process in accordance with claim 18 wherein said macrolactamization coupling agent comprises one or more members selected from the group consisting of 1-(3-dimethylaminopropyl)-3-ethylcarbodiimide hydrochloride, 1-(3-dimethylaminopropyl)-3-ethylcarbodiimide hydrochloride and 1-hydroxy-7-benzotriazole hydrate, 1-(3-dimethylaminopropyl)-3-ethylcarbodiimide hydrochloride and 1-hydroxy-7-azabenzotriazole hydrate, dicyclohexylcarbodiimide, diisopropylcarbodiimide, diphenylphosphoryl azide, O-benzotriazol-1-yl-N,N,N',N'-bis(tetramethylene)uronium hexafluorophosphate, O-(7-azabenzotriazol)-1-yl-N,N,N',N'-bis(tetramethylene)uronium hexafluorophosphate, benzotriazol-1-yloxy-tris(bimethylamino)phosphonium hexafluorophosphate, N,N-dimethyl-4-aminopyridine, $K_2CO_3$, diisopropylamine, and triethylamine.

28. A process in accordance with claim 27 where said coupling agent is 1-(3-dimethylaminopropyl)-3-ethylcarbodiimide hydrochloride and 1-hydroxy-7-benzotriazole hydrate.

* * * * *

UNITED STATES PATENT AND TRADEMARK OFFICE
CERTIFICATE OF CORRECTION

PATENT NO.    : 6,518,421 B1                                    Page 1 of 1
DATED         : February 11, 2003
INVENTOR(S)   : Li et al.

It is certified that error appears in the above-identified patent and that said Letters Patent is hereby corrected as shown below:

Column 16, lines 28-35, the formula:

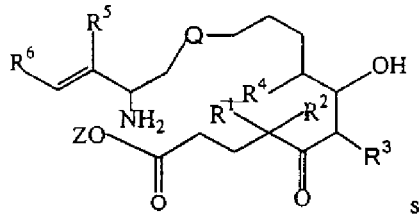 should read 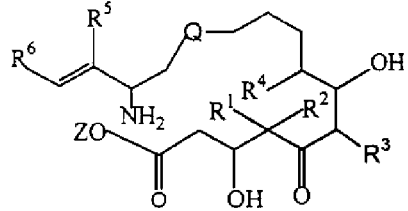

Column 19, lines 5-13, the formula:

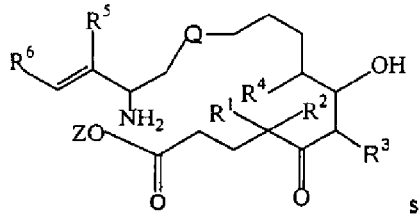 should read 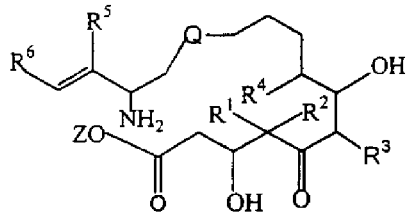

Column 23, lines 6-14, the formula:

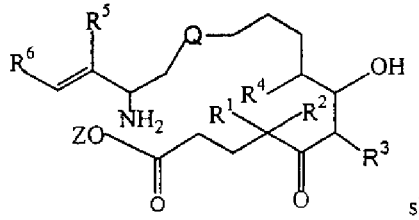 should read 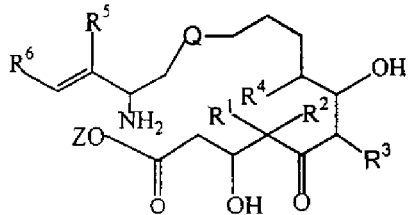

Signed and Sealed this

Twelfth Day of October, 2004

JON W. DUDAS
*Director of the United States Patent and Trademark Office*